(12) United States Patent
Lattanzio et al.

(10) Patent No.: US 10,734,098 B2
(45) Date of Patent: Aug. 4, 2020

(54) CATALYTIC DEHYDROGENATION CATALYST HEALTH INDEX

(71) Applicant: UOP LLC, Des Plaines, IL (US)

(72) Inventors: Louis A. Lattanzio, Mount Prospect, IL (US); Abhishek Pednekar, Schaumburg, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/363,406

(22) Filed: Mar. 25, 2019

(65) Prior Publication Data

US 2019/0304572 A1    Oct. 3, 2019

Related U.S. Application Data

(60) Provisional application No. 62/650,618, filed on Mar. 30, 2018.

(51) Int. Cl.
*G08B 21/00*    (2006.01)
*G16C 20/10*    (2019.01)
(Continued)

(52) U.S. Cl.
CPC .............. *G16C 20/10* (2019.02); *C07C 5/333* (2013.01); *C10G 29/00* (2013.01); *C10G 35/04* (2013.01);
(Continued)

(58) Field of Classification Search
CPC ........ G16C 20/10; C07C 5/333; C10G 29/00; C10G 35/04; C10G 35/24
See application file for complete search history.

(56) References Cited

U.S. PATENT DOCUMENTS

| | | | |
|---|---|---|---|
| 4,159,239 A | 6/1979 | Schwartz | 208/113 |
| 4,267,458 A | 5/1981 | Uram | 290/40 R |

(Continued)

FOREIGN PATENT DOCUMENTS

| | | | |
|---|---|---|---|
| EP | 0181744 A1 | 5/1986 | B65G 53/66 |
| EP | 2746884 A1 | 6/2014 | G05B 23/02 |

(Continued)

OTHER PUBLICATIONS

Bespalov A. V. et al., Control systems of chemical and technological processes, pp. 508-509 (2001) (Russian).

(Continued)

*Primary Examiner* — Phung Nguyen

(57) ABSTRACT

Methods, systems, and apparatuses for monitoring health of a catalyst in a plant by retrieving plant data, comparing the plant data to equilibrium conditions, and sending a notification comprising an indication of the health of the catalyst. A plant may be configured to produce a product using a catalyst. A plant monitoring computing platform may be configured to receive, from sensors and/or computing devices of the plant, plant data and/or lab data corresponding to the catalyst. The plant monitoring computing platform may determine equilibrium conditions corresponding to the plant. Based on a comparison of the plant data, the equilibrium conditions, and/or target equilibrium conditions, the plant monitoring computing platform may send a notification. The notification may comprise an indication of the performance of the catalyst.

20 Claims, 5 Drawing Sheets

(51) Int. Cl.
*C10G 29/00* (2006.01)
*C07C 5/333* (2006.01)
*C10G 35/24* (2006.01)
*C10G 35/04* (2006.01)

(52) U.S. Cl.
CPC ..... *C10G 35/24* (2013.01); *C10G 2300/1081* (2013.01); *C10G 2300/70* (2013.01); *C10G 2400/20* (2013.01); *C10G 2400/22* (2013.01)

(56) References Cited

U.S. PATENT DOCUMENTS

| | | | |
|---|---|---|---|
| 4,284,494 A | 8/1981 | Bartholic | 208/164 |
| 4,362,614 A | 12/1982 | Asdigian | 208/235 |
| 4,380,146 A | 4/1983 | Yannone | 60/39.281 |
| 4,385,985 A | 5/1983 | Gross | 208/113 |
| 4,411,773 A | 10/1983 | Gross | 208/159 |
| 4,709,546 A | 12/1987 | Weiler | 415/116 |
| 4,775,460 A | 10/1988 | Reno | |
| 4,795,545 A | 1/1989 | Schmidt | |
| 4,902,469 A | 2/1990 | Watson | 376/216 |
| 5,077,252 A | 12/1991 | Owen et al. | 502/43 |
| 5,227,121 A | 7/1993 | Scarola | 340/525 |
| 5,582,684 A | 12/1996 | Holmqvist et al. | 162/49 |
| 5,605,435 A | 2/1997 | Haugen | 137/514 |
| 5,616,214 A | 4/1997 | Leclerc | 162/49 |
| 5,642,296 A | 6/1997 | Saxena | 216/84 |
| 5,666,297 A | 9/1997 | Britt et al. | 364/578 |
| 5,817,517 A | 10/1998 | Perry et al. | 436/55 |
| 6,038,540 A | 3/2000 | Krist et al. | 705/8 |
| 6,081,230 A | 6/2000 | Hoshino | 342/357.32 |
| 6,230,486 B1 | 5/2001 | Yasui | 123/674 |
| 6,266,605 B1 | 7/2001 | Yasui | 60/276 |
| 6,271,845 B1 | 8/2001 | Richardson | 715/764 |
| 6,392,114 B1 | 5/2002 | Shields et al. | 582/719 |
| 6,760,716 B1 | 7/2004 | Ganesamoorthi et al. | 706/21 |
| 6,772,044 B1 | 8/2004 | Mathur et al. | 700/204 |
| 6,795,798 B2 | 9/2004 | Eryurek et al. | 702/188 |
| 6,982,032 B2 | 1/2006 | Shaffer et al. | 210/101 |
| 6,983,227 B1 | 1/2006 | Thalhammer-Reyero | |
| 7,006,889 B2 | 2/2006 | Mathur et al. | 700/204 |
| 7,067,333 B1 | 6/2006 | Pasadyn et al. | 438/5 |
| 7,133,807 B2 | 11/2006 | Karasawa | 702/188 |
| 7,151,966 B1 | 12/2006 | Baier et al. | 700/19 |
| 7,246,039 B2 | 7/2007 | Moorhouse | 702/185 |
| 7,313,447 B2 | 12/2007 | Hsuing et al. | 700/9 |
| 7,415,357 B1 | 8/2008 | Stluka et al. | 702/6 |
| 7,567,887 B2 * | 7/2009 | Emigholz | C10G 11/18 702/182 |
| 7,742,833 B1 | 6/2010 | Herbst et al. | 700/108 |
| 7,836,941 B2 | 11/2010 | Song et al. | |
| 7,877,596 B2 | 1/2011 | Foo Kune et al. | 713/153 |
| 7,925,979 B2 | 4/2011 | Forney et al. | 715/733 |
| 7,936,878 B2 | 5/2011 | Kune et al. | 380/270 |
| 7,979,192 B2 | 7/2011 | Morrison et al. | |
| 7,995,526 B2 | 8/2011 | Liu et al. | 370/329 |
| 8,050,889 B2 | 11/2011 | Fluegge et al. | 702/182 |
| 8,055,371 B2 | 11/2011 | Sanford et al. | 700/108 |
| 8,111,619 B2 | 2/2012 | Liu et al. | 370/229 |
| 8,128,808 B2 | 3/2012 | Hassan et al. | 208/209 |
| 8,204,717 B2 | 6/2012 | McLaughlin et al. | 702/188 |
| 8,244,384 B2 | 8/2012 | Pachner et al. | 700/30 |
| 8,280,057 B2 | 10/2012 | Budampati et al. | 380/270 |
| 8,352,049 B2 | 1/2013 | Hsiung et al. | |
| 8,354,081 B2 | 1/2013 | Wheat et al. | |
| 8,385,436 B2 | 2/2013 | Holm et al. | 375/260 |
| 8,428,067 B2 | 4/2013 | Budampati et al. | 370/395.21 |
| 8,458,778 B2 | 6/2013 | Budampati et al. | 726/6 |
| 8,571,064 B2 | 10/2013 | Kore et al. | 370/469 |
| 8,630,962 B2 | 1/2014 | Maeda | 706/12 |
| 8,644,192 B2 | 2/2014 | Budampati et al. | 370/255 |
| 8,811,231 B2 | 8/2014 | Budampati et al. | 370/255 |
| 8,815,152 B2 | 8/2014 | Burgess et al. | |
| 8,923,882 B2 | 12/2014 | Gandhi et al. | 455/455 |
| 8,926,737 B2 | 1/2015 | Chatterjee et al. | |
| 9,053,260 B2 | 6/2015 | Romatier et al. | |
| 9,134,717 B2 | 9/2015 | Trnka | |
| 9,166,667 B2 | 10/2015 | Thanikachalam | |
| 9,176,498 B2 | 11/2015 | Baramov | |
| 9,354,631 B2 | 5/2016 | Mohideen et al. | |
| 9,571,919 B2 | 2/2017 | Zhang et al. | |
| 9,580,341 B1 | 2/2017 | Brown et al. | C02F 3/006 |
| 9,751,817 B2 | 9/2017 | Jani et al. | |
| 9,864,823 B2 | 1/2018 | Horn et al. | |
| 9,968,899 B1 | 5/2018 | Gellaboina et al. | |
| 10,095,200 B2 | 10/2018 | Horn et al. | |
| 10,107,295 B1 | 10/2018 | Brecheisen | |
| 10,180,680 B2 | 1/2019 | Horn et al. | |
| 10,183,266 B2 | 1/2019 | Victor et al. | |
| 10,222,787 B2 | 3/2019 | Romatier et al. | |
| 10,328,408 B2 | 6/2019 | Victor et al. | |
| 2002/0123864 A1 | 9/2002 | Eryurek et al. | 702/188 |
| 2002/0179495 A1 | 12/2002 | Heyse et al. | 208/137 |
| 2003/0036052 A1 | 2/2003 | Delwiche et al. | 435/4 |
| 2003/0105775 A1 | 6/2003 | Shimada | |
| 2003/0147351 A1 | 8/2003 | Greenlee | 370/232 |
| 2003/0223918 A1 | 12/2003 | Cammy | 422/144 |
| 2004/0079392 A1 | 4/2004 | Kuechler | 134/22.19 |
| 2004/0099572 A1 | 5/2004 | Evans | 208/113 |
| 2004/0109788 A1 | 6/2004 | Li et al. | 422/3 |
| 2004/0122273 A1 | 6/2004 | Kabin | 585/639 |
| 2004/0122936 A1 | 6/2004 | Mizelle et al. | |
| 2004/0147036 A1 | 7/2004 | Krenn et al. | 436/119 |
| 2004/0148144 A1 | 7/2004 | Martin | |
| 2004/0204775 A1 | 10/2004 | Keyes | 705/30 |
| 2004/0204913 A1 | 10/2004 | Mueller et al. | |
| 2004/0220689 A1 | 11/2004 | Mathur et al. | 700/97 |
| 2004/0220778 A1 | 11/2004 | Imai et al. | 702/188 |
| 2005/0027721 A1 | 2/2005 | Saenz | 707/100 |
| 2005/0029163 A1 | 2/2005 | Letzsch | 208/113 |
| 2005/0098033 A1 | 5/2005 | Mallavarapu et al. | 95/96 |
| 2005/0133211 A1 | 6/2005 | Osborn et al. | |
| 2005/0216209 A1 | 9/2005 | Evans | 702/45 |
| 2006/0020423 A1 | 1/2006 | Sharpe, Jr. | 702/183 |
| 2006/0133412 A1 | 6/2006 | Callaghan | 370/465 |
| 2006/0252642 A1 | 11/2006 | Kanazirev | |
| 2006/0259163 A1 | 11/2006 | Hsiung et al. | 700/30 |
| 2007/0020154 A1 | 1/2007 | Evans | 422/139 |
| 2007/0059159 A1 | 3/2007 | Hjerpe | 415/117 |
| 2007/0059838 A1 | 3/2007 | Morrison et al. | 436/55 |
| 2007/0091824 A1 | 4/2007 | Budampati et al. | 370/255 |
| 2007/0091825 A1 | 4/2007 | Budampati et al. | 370/255 |
| 2007/0185664 A1 | 8/2007 | Tanaka | 702/56 |
| 2007/0192078 A1 | 8/2007 | Nasle et al. | 703/14 |
| 2007/0212790 A1 | 9/2007 | Welch et al. | 436/139 |
| 2007/0250292 A1 | 10/2007 | Alagappan et al. | 702/184 |
| 2007/0260656 A1 | 11/2007 | Wiig | |
| 2007/0271452 A1 | 11/2007 | Foo Kune et al. | 713/150 |
| 2008/0086322 A1 | 4/2008 | Wallace | 705/1 |
| 2008/0130902 A1 | 6/2008 | Foo Kune et al. | 380/286 |
| 2008/0154434 A1 | 6/2008 | Galloway et al. | |
| 2008/0217005 A1 | 9/2008 | Stluka et al. | 166/250.01 |
| 2008/0282606 A1 | 11/2008 | Plaza et al. | |
| 2009/0059786 A1 | 3/2009 | Budampati et al. | 370/230 |
| 2009/0060192 A1 | 3/2009 | Budampati et al. | 380/270 |
| 2009/0064295 A1 | 3/2009 | Budampati et al. | 726/6 |
| 2009/0149981 A1 * | 6/2009 | Evans | G05B 23/0254 700/110 |
| 2009/0201899 A1 | 8/2009 | Liu et al. | 370/338 |
| 2009/0204245 A1 | 8/2009 | Sustaeta | 700/99 |
| 2009/0245286 A1 | 10/2009 | Kore et al. | 370/475 |
| 2009/0268674 A1 | 10/2009 | Liu et al. | 370/329 |
| 2009/0281677 A1 | 11/2009 | Botich | 700/295 |
| 2010/0014599 A1 | 1/2010 | Holm et al. | 375/260 |
| 2010/0108567 A1 | 5/2010 | Medoff | 208/49 |
| 2010/0125347 A1 | 5/2010 | Martin et al. | 700/31 |
| 2010/0152900 A1 | 6/2010 | Gurciullo et al. | |
| 2010/0158764 A1 | 6/2010 | Hedrick | 422/134 |
| 2010/0230324 A1 | 9/2010 | Al-Alloush et al. | 208/82 |
| 2010/0262900 A1 | 10/2010 | Romatier et al. | 715/219 |
| 2011/0112659 A1 | 5/2011 | Pachner et al. | 700/29 |
| 2011/0152590 A1 | 6/2011 | Sadler et al. | 585/313 |
| 2011/0152591 A1 | 6/2011 | Sadler et al. | 585/313 |
| 2011/0311014 A1 | 12/2011 | Hottovy et al. | 376/283 |

(56) References Cited

U.S. PATENT DOCUMENTS

| | | |
|---|---|---|
| 2012/0029966 A1 | 2/2012 | Cheewakriengkrai et al. ............ 705/7.25 |
| 2012/0083933 A1 | 4/2012 | Subbu et al. ................ 700/291 |
| 2012/0095808 A1 | 4/2012 | Kattapuram et al. ........ 705/7.37 |
| 2012/0104295 A1 | 5/2012 | Do et al. ................. 251/129.01 |
| 2012/0121376 A1 | 5/2012 | Huis in Het Veld ............ 415/1 |
| 2012/0123583 A1 | 5/2012 | Hazen et al. |
| 2012/0197616 A1 | 8/2012 | Trnka ............................... 703/6 |
| 2012/0259583 A1 | 10/2012 | Noboa et al. |
| 2013/0029587 A1 | 1/2013 | Gandhi et al. ..................... 455/7 |
| 2013/0031960 A1 | 2/2013 | Delrahim et al. ......... 73/40.5 R |
| 2013/0079899 A1 | 3/2013 | Baramov ........................ 700/32 |
| 2013/0090088 A1 | 4/2013 | Chevsky et al. .............. 455/411 |
| 2013/0094422 A1 | 4/2013 | Thanikachalam ............ 370/312 |
| 2013/0172643 A1 | 7/2013 | Pradeep ........................ 585/310 |
| 2013/0253898 A1 | 9/2013 | Meagher et al. ............... 703/18 |
| 2013/0270157 A1 | 10/2013 | Ferrara .................... 208/48 AA |
| 2013/0311437 A1 | 11/2013 | Stluka et al. .................. 707/706 |
| 2013/0327052 A1 | 12/2013 | O'Neill et al. .................. 60/772 |
| 2014/0008035 A1 | 1/2014 | Patankar et al. |
| 2014/0026598 A1 | 1/2014 | Trawicki ........................... 62/56 |
| 2014/0074273 A1 | 3/2014 | Mohideen et al. ............. 700/98 |
| 2014/0114039 A1 | 4/2014 | Benham et al. .......... 526/348.5 |
| 2014/0131027 A1 | 5/2014 | Chir ................ 165/300 |
| 2014/0163275 A1 | 6/2014 | Yanagawa et al. ........... 585/319 |
| 2014/0179968 A1 | 6/2014 | Yanagawa et al. ........... 585/476 |
| 2014/0212978 A1 | 7/2014 | Sharpe, Jr. et al. ............... 436/6 |
| 2014/0294683 A1 | 10/2014 | Siedler ......................... 422/129 |
| 2014/0294684 A1 | 10/2014 | Siedler ......................... 422/129 |
| 2014/0296058 A1 | 10/2014 | Sechrist et al. ................. 502/53 |
| 2014/0309756 A1 | 10/2014 | Trygstad ........................ 700/31 |
| 2014/0337256 A1 | 11/2014 | Varadi et al. ................... 706/12 |
| 2014/0337277 A1 | 11/2014 | Asenjo et al. |
| 2015/0059714 A1 | 3/2015 | Bernards .................. 123/568.11 |
| 2015/0060331 A1 | 3/2015 | Sechrist et al. |
| 2015/0077263 A1 | 3/2015 | Ali et al. ....................... 340/679 |
| 2015/0078970 A1 | 3/2015 | Iddir et al. .................... 422/218 |
| 2015/0098862 A1 | 4/2015 | Lok et al. ........................ 422/49 |
| 2015/0158789 A1 | 6/2015 | Keusenkothen |
| 2015/0185716 A1 | 7/2015 | Wichmann et al. .......... 700/287 |
| 2015/0276208 A1 | 10/2015 | Maturana et al. ............ 700/274 |
| 2015/0284641 A1 | 10/2015 | Shi ................ 208/113 |
| 2015/0330571 A1 | 11/2015 | Beuneken ........................ 141/4 |
| 2015/0358091 A1* | 12/2015 | Sappok .................. H04B 17/00 455/67.11 |
| 2016/0033941 A1 | 2/2016 | T et al. .......................... 700/81 |
| 2016/0048119 A1 | 2/2016 | Wojsznis ........................ 700/11 |
| 2016/0098037 A1 | 4/2016 | Zornio et al. ................... 700/20 |
| 2016/0098234 A1 | 4/2016 | Weaver ........................ 358/1.15 |
| 2016/0122663 A1 | 5/2016 | Pintart et al. |
| 2016/0147204 A1 | 5/2016 | Wichmann et al. .......... 700/287 |
| 2016/0237910 A1 | 8/2016 | Saito |
| 2016/0260041 A1 | 9/2016 | Horn et al. |
| 2016/0291584 A1 | 10/2016 | Horn et al. |
| 2016/0292188 A1 | 10/2016 | Horn et al. |
| 2016/0292325 A1 | 10/2016 | Horn et al. |
| 2016/0313653 A1 | 10/2016 | Mink |
| 2016/0363315 A1 | 12/2016 | Colannino et al. |
| 2017/0009932 A1 | 1/2017 | Oh |
| 2017/0058213 A1 | 3/2017 | Oprins ........................... 585/303 |
| 2017/0082320 A1 | 3/2017 | Wang |
| 2017/0107188 A1 | 4/2017 | Kawaguchi |
| 2017/0284410 A1 | 10/2017 | Sharpe, Jr. |
| 2017/0315543 A1 | 11/2017 | Horn et al. |
| 2017/0323038 A1 | 11/2017 | Horn et al. |
| 2017/0352899 A1 | 12/2017 | Asai |
| 2018/0046155 A1 | 2/2018 | Horn et al. |
| 2018/0081344 A1 | 3/2018 | Romatier et al. |
| 2018/0082569 A1 | 3/2018 | Horn et al. |
| 2018/0121581 A1 | 5/2018 | Horn et al. |
| 2018/0122021 A1 | 5/2018 | Horn et al. |
| 2018/0155638 A1 | 6/2018 | Al-Ghamdi ..................... 208/79 |
| 2018/0155642 A1 | 6/2018 | Al-Ghamdi et al. |
| 2018/0197350 A1 | 7/2018 | Kim |
| 2018/0275690 A1 | 9/2018 | Lattanzio et al. |
| 2018/0275691 A1 | 9/2018 | Lattanzio et al. |
| 2018/0275692 A1 | 9/2018 | Lattanzio et al. |
| 2018/0280914 A1 | 10/2018 | Victor et al. |
| 2018/0280917 A1 | 10/2018 | Victor et al. |
| 2018/0282633 A1 | 10/2018 | Van de Cotte et al. |
| 2018/0282634 A1 | 10/2018 | Van de Cotte et al. |
| 2018/0282635 A1 | 10/2018 | Van de Cotte et al. |
| 2018/0283368 A1 | 10/2018 | Van de Cotte et al. |
| 2018/0283392 A1 | 10/2018 | Van de Cotte et al. |
| 2018/0283404 A1 | 10/2018 | Van de Cotte et al. |
| 2018/0283811 A1 | 10/2018 | Victor et al. |
| 2018/0283812 A1 | 10/2018 | Victor et al. |
| 2018/0283813 A1 | 10/2018 | Victor et al. |
| 2018/0283815 A1 | 10/2018 | Victor et al. |
| 2018/0283816 A1 | 10/2018 | Victor et al. |
| 2018/0283818 A1 | 10/2018 | Victor et al. |
| 2018/0284705 A1 | 10/2018 | Van de Cotte et al. |
| 2018/0286141 A1 | 10/2018 | Van de Cotte et al. |
| 2018/0311609 A1 | 11/2018 | McCool et al. |
| 2018/0362862 A1 | 12/2018 | Gellaboina et al. |
| 2018/0363914 A1 | 12/2018 | Faiella et al. |
| 2018/0364747 A1 | 12/2018 | Charr et al. |
| 2019/0002318 A1 | 1/2019 | Thakkar et al. |
| 2019/0003978 A1 | 1/2019 | Shi et al. |
| 2019/0015806 A1 | 1/2019 | Gellaboina et al. |
| 2019/0041813 A1 | 2/2019 | Horn et al. |
| 2019/0083920 A1 | 3/2019 | Bjorklund et al. |
| 2019/0101336 A1 | 4/2019 | Victor et al. |
| 2019/0101342 A1 | 4/2019 | Victor et al. |
| 2019/0101907 A1 | 4/2019 | Charr et al. |
| 2019/0102966 A1 | 4/2019 | Lorenz |
| 2019/0108454 A1 | 4/2019 | Banerjee et al. |
| 2019/0120810 A1 | 4/2019 | Kumar KN et al. |
| 2019/0151814 A1 | 5/2019 | Victor et al. |
| 2019/0155259 A1 | 5/2019 | Romatier et al. |

FOREIGN PATENT DOCUMENTS

| | | | | |
|---|---|---|---|---|
| EP | 2801937 A1 | 11/2014 | ............ G06Q 10/06 |
| GB | 1134439 A | 11/1968 | ............ G01N 31/22 |
| WO | WO 1990/010083 A1 | 9/1990 | ............... C12Q 1/04 |
| WO | WO 2001/060951 A1 | 8/2001 | ............ C10G 51/04 |
| WO | WO 2006/044408 A1 | 4/2006 | ............ F23D 14/72 |
| WO | WO 2007/095585 A2 | 8/2007 | ........... A61K 31/721 |
| WO | WO 2009/046095 A1 | 4/2009 | ............ G06F 11/00 |
| WO | WO 2014/042508 A1 | 3/2014 | ............ G06Q 50/04 |
| WO | WO 2014/123993 A1 | 8/2014 | ............ G06F 17/00 |
| WO | WO 2016/141128 A1 | 9/2016 | ............ G06Q 10/06 |
| WO | WO 2017/079058 A1 | 5/2017 | ............ B01D 1/14 |

OTHER PUBLICATIONS

Daniel Goebel, Dry Gas Seal Contamination During Operation and Pressurization Hold, [online], Feb. 2016, [retrieved on Jun. 19, 2019]. Retrieved from <https ://core.ac.uk/download/pdf/84815277. pdf> (Year: 2016).

EnergyMEDOR®, Product brochure (Nov. 2014).

Chistof Huber, Density and Concentration Measurement Application for Novel MEMS-based Micro Densitometer for Gas, [online], 2016, [retrieved on Jun. 19, 2016]. Retrieved from <https://www.ama-science.org/proceedings/getFile/ZwZ1 BD==> (Year: 2016).

Lotters, Real-time Composition Determination of Gas Mixtures, [online], 2015, [retrieved on Jun. 19, 2019]. Retrieved from <https://www.ama-science.org/proceedings/getFile/ZwNOZj==>(Year: 2015).

Maybeck, Peter S., "Stochastic models, estimation, and control," vol. 1, Academic Press (1979), 19 pages.

* cited by examiner

CATALYTIC DEHYDROGENATION CATALYST HEALTH INDEX

CROSS REFERENCE TO RELATED APPLICATIONS

This application is a non-provisional of, and claims priority to, U.S. Provisional Application No. 62/650,618, filed Mar. 30, 2018, which is incorporated by reference herein in its entirety for all purposes.

FIELD

The present disclosure is related to a method and system for managing the operation of a plant, such as a chemical plant or a petrochemical plant or a refinery, and more particularly to a method for improving operations in a plant that uses a catalyst. Typical plants may be those that provide catalytic dehydrogenation or hydrocarbon cracking, or catalytic reforming, or other process units.

BACKGROUND

A plant or refinery may use a catalyst along with a reactant to produce a product, such as a product gas. Over time, the performance of the catalyst may degrade. A plant or refinery might not have the ability to track catalyst health on a regular basis, but rather may rely on external periodic testing of a catalyst. As such, a plant or refinery may have difficulty planning if and when to change a catalyst and/or modify operating conditions of the catalyst in view of catalyst health. Moreover, if a problem occurs and a catalyst is deactivated, it is often too late to take remedial action to improve the health of the catalyst. There is thus an ongoing need to improve tracking the catalyst health.

SUMMARY

The following summary presents a simplified summary of certain features. The summary is not an extensive overview and is not intended to identify key or critical elements.

One or more embodiments may include methods, computing devices, or systems for receiving plant data from a plant using a catalyst to produce a product and, based on the plant data received, determining the health of the catalyst. A plant monitoring computing platform may be configured to receive plant data from a plant. The plant may be configured to use a catalyst with a reactant to produce a product. The plant may be further configured with one or more sensors and computing devices that report measurements to the plant monitoring computing platform. Based on the plant data, the plant monitoring computing platform may determine equilibrium conditions for the plant. The plant monitoring computing platform may modify the equilibrium conditions based on, for example, a machine learning algorithm or operator input. The plant monitoring computing platform may compare plant data to the equilibrium conditions. Based on the comparison, the plant monitoring computing platform may trigger a notification. The notification may comprise an indication of the health of the catalyst.

Other technical features may be readily apparent to one skilled in the art from the following figures, descriptions, and claims.

BRIEF DESCRIPTION OF DRAWINGS

The present disclosure is illustrated by way of example and not limited in the accompanying figures in which like reference numerals indicate similar elements and in which.

DETAILED DESCRIPTION

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure.

It is noted that various connections between elements are discussed in the following description. It is noted that these connections are general and, unless specified otherwise, may be direct or indirect, wired or wireless, and that the specification is not intended to be limiting in this respect.

Chemical Plants and Catalysts

As a general introduction, chemical plants, petrochemical plants, and/or refineries may include one or more pieces of equipment that process one or more input chemicals to create one or more products. For example, catalytic dehydrogenation can be used to convert paraffins to the corresponding olefin, e.g., propane to propene, or butane to butene. To produce one or more products, a chemical plant or a petrochemical plant or a refinery may use catalysts. A catalyst is a substance that may be used in particular conditions (e.g., at a particular temperature, with a particular reactant, and/or in a particular quantity) to produce a chemical reaction and to produce a product. For example, naphtha, derived from crude oil, may undergo multiple processes using multiple catalysts to ultimately become a product such as gasoline. Virtually all portions of a chemical plants, petrochemical plants, and/or refineries wear down with age, and catalysts are no exception. In the process of producing a product, a catalyst may be consumed, become inactive, and/or may otherwise be expended over time. Operators of chemical plants, petrochemical plants, and/or refineries must therefore rejuvenate and/or replace catalysts in order to maintain peak operational efficiency.

References herein to a "plant" are to be understood to refer to any of various types of chemical and petrochemical manufacturing or refining facilities. References herein to a plant "operators" are to be understood to refer to and/or include, without limitation, plant planners, managers, engineers, technicians, and others interested in, overseeing, and/or running the daily operations at a plant.

Figure 1:
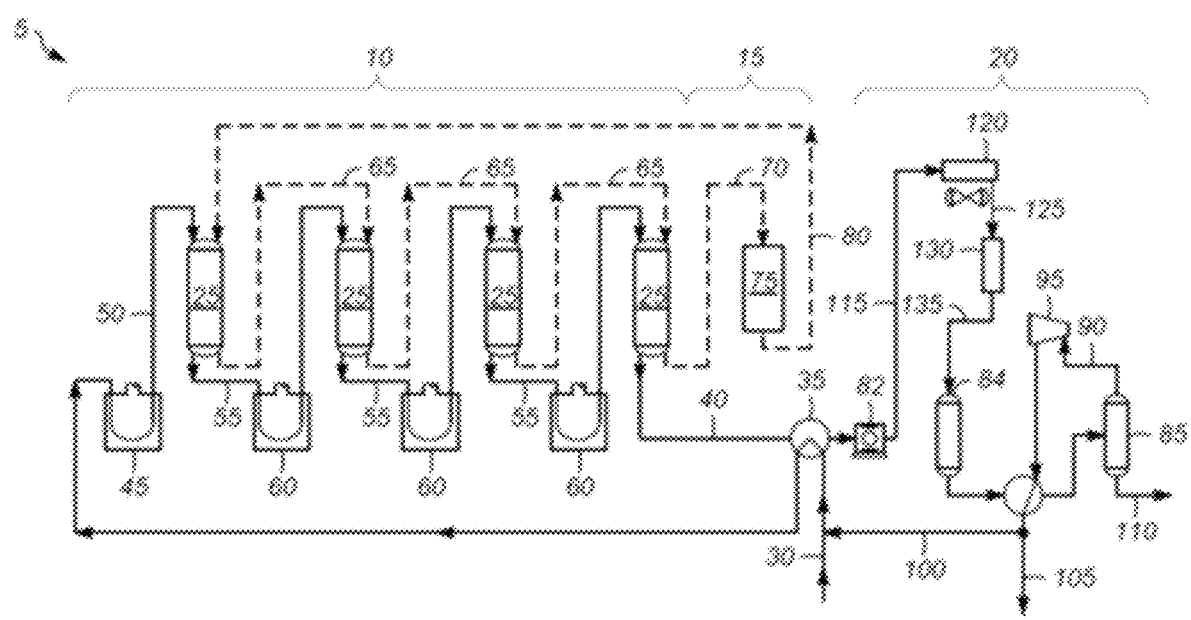
FIG. 1 shows an example catalytic dehydrogenation process in accordance with one or more example embodiments.

FIG. 1 shows an example of a catalytic dehydrogenation process 5. The process 5 includes a reactor section 10, a catalyst regeneration section 15, and a product recovery section 20.

The reactor section 10 includes one or more reactors 25. A hydrocarbon feed 30 is sent to a heat exchanger 35 where it exchanges heat with a reactor effluent 40 to raise the feed temperature. The hydrocarbon feed 30 is sent to a preheater 45 where it is heated to the desired inlet temperature. The preheated feed 50 is sent from the preheater 45 to the first reactor 25. Because the dehydrogenation reaction is endothermic, the temperature of the effluent 55 from the first reactor 25 is less than the temperature of the preheated feed 50. The effluent 55 is sent to interstage heaters 60 to raise the temperature to the desired inlet temperature for the next reactor 25.

After the last reactor, the reactor effluent 40 is sent to the heat exchanger 35, and heat is exchanged with the feed 30. The reactor effluent 40 is then sent to the product recovery section 20. The catalyst 65 moves through the series of reactors 25. When the catalyst 70 leaves the last reactor 25, it is sent to the catalyst regeneration section 15. The catalyst regeneration section 15 includes a regenerator 75 where coke on the catalyst is burned off and the catalyst may go through a reconditioning step. A regenerated catalyst 80 is sent back to the first reactor 25.

The reactor effluent 40 is compressed in the compressor or centrifugal compressor 82. The compressed effluent 115 is introduced to a cooler 120, for instance a heat exchanger. The cooler 120 lowers the temperature of the compressed effluent. The cooled effluent 125 (cooled product stream) is then introduced into a chloride remover 130, such as a chloride scavenging guard bed. The chloride remover 130 includes an adsorbent, which adsorbs chlorides from the cooled effluent 125 and provides a treated effluent 135. Treated effluent 135 is introduced to a drier 84.

The dried effluent is separated in separator 85. Gas 90 is expanded in expander 95 and separated into a recycle hydrogen stream 100 and a net separator gas stream 105. A liquid stream 110, which includes the olefin product and unconverted paraffin, is sent for further processing, where the desired olefin product is recovered and the unconverted paraffin is recycled to the dehydrogenation reactor 25.

Figure 2:
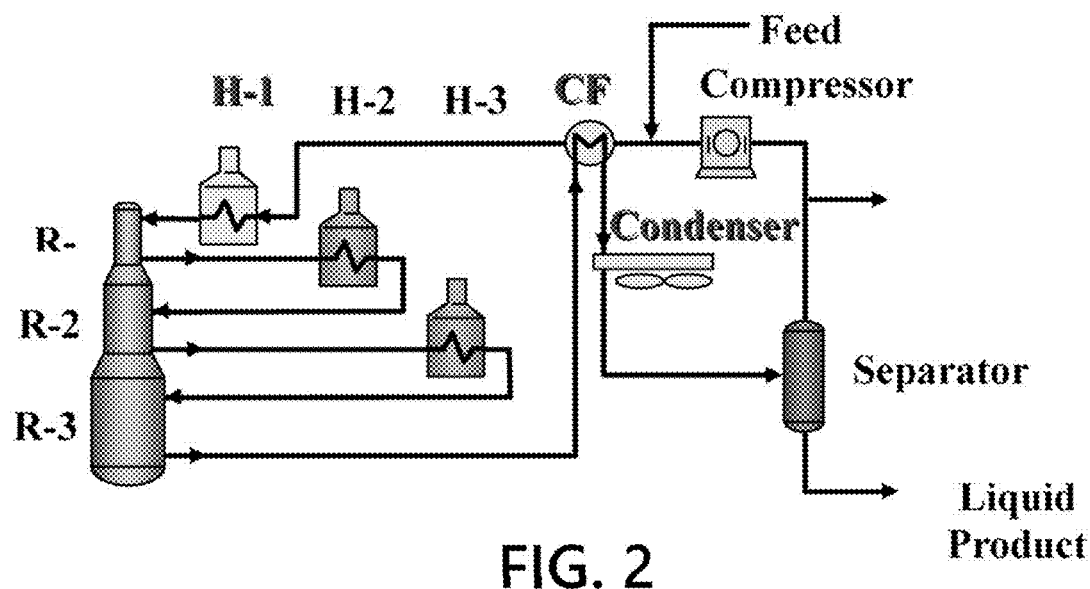
FIG. 2 depicts an illustrative catalytic reforming process using a (vertically-oriented) combined feed-effluent (CFE) exchanger in accordance with one or more example embodiments.

FIG. 2 shows an example of a process for reforming with continuous catalyst regeneration (CCR) using a (vertically oriented) combined feed-effluent (CFE) exchanger. The cold stream, a combination of liquid feed with hydrogen rich recycle gas (e.g., light paraffins), is introduced into a CFE exchanger where the feed is vaporized. The feed/recycle exits the CFE as a gas and goes through a series of heating and reaction steps. The resulting product effluent or hot stream is introduced into the CFE exchanger and is cooled down. The effluent exits the CFE exchanger and is then cooled down further and condensed using an air cooler. The liquid product is separated from the gas stream containing hydrogen and light paraffins. Some of the gas stream is removed, for example as a product, and the rest of the stream is used as recycle gas.

Figure 3:
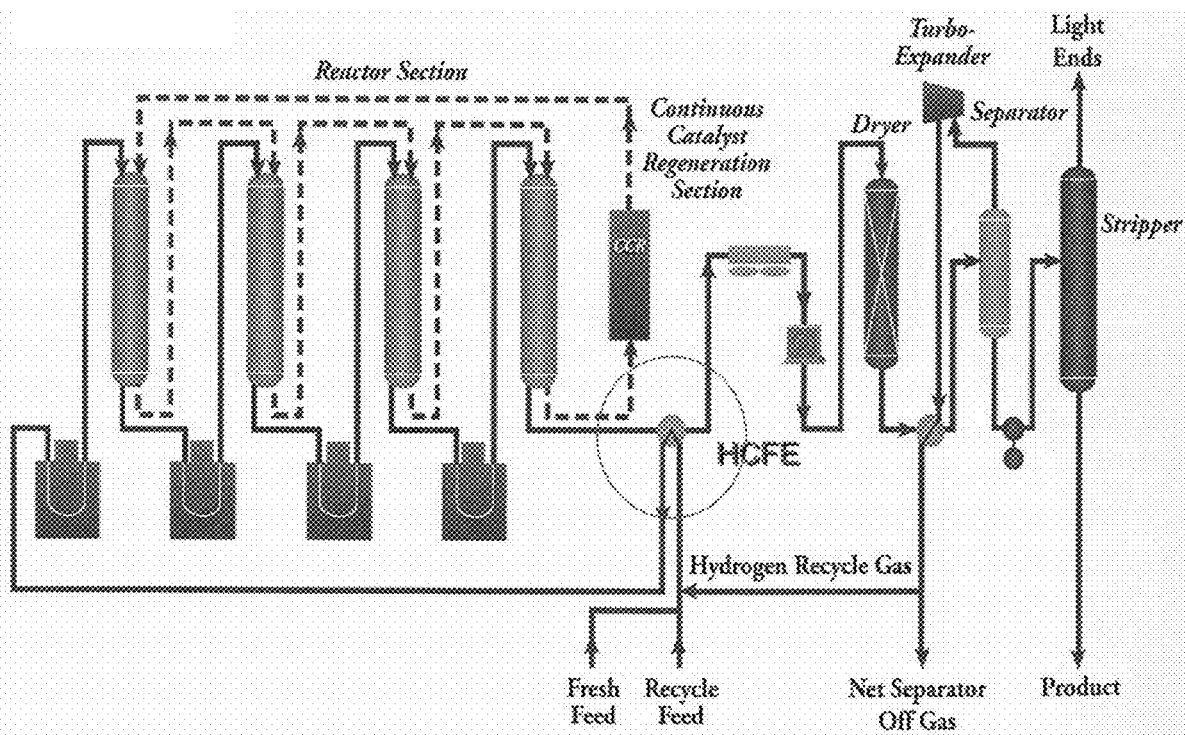
FIG. 3 depicts an illustrative OLEFLEX process (catalytic dehydrogenation) with continuous catalyst regeneration (CCR) using a (vertically-oriented) hot combined feed-effluent (HCFE) exchanger in accordance with one or more example embodiments.

FIG. 3 shows a catalytic dehydrogenation process (e.g., an OLEFLEX process) with continuous catalyst regeneration (CCR) using a (vertically-oriented) hot combined feed-effluent (HCFE) exchanger. The cold stream, a combination of vapor feed with hydrogen rich recycle gas, is introduced into a HCFE exchanger and is heated. The feed/recycle exits the HCFE as a gas and goes through a series of heating and reaction steps. The resulting product effluent or hot stream is introduced into the HCFE exchanger and is cooled down. The effluent exits the HCFE exchanger and is then cooled down further using an air cooler. The effluent then passes through a dryer, separators, and strippers. Hydrogen recycle gas is separated after the dryer and returned to the feed stream.

Monitoring of Plant Operating Conditions

Figure 4:
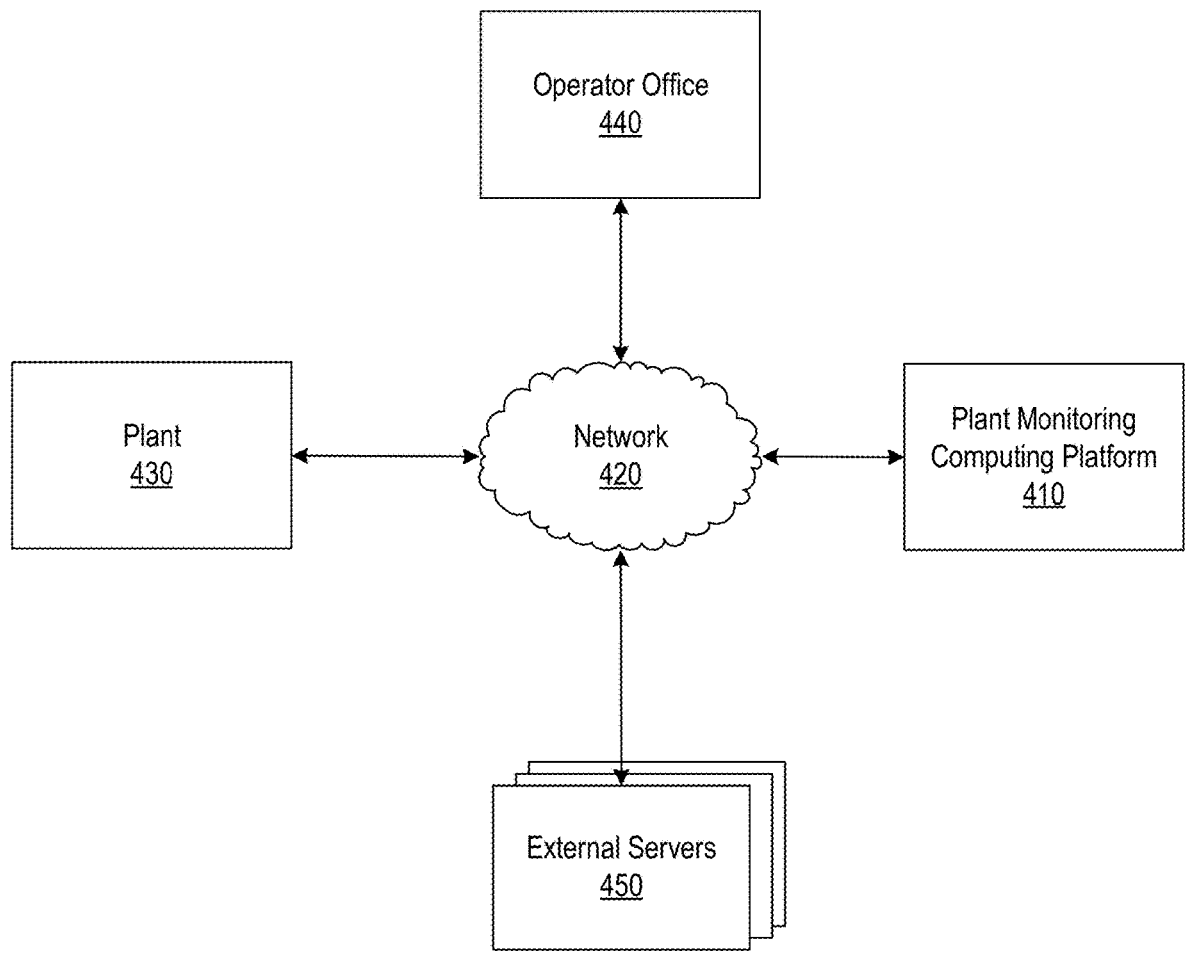
FIG. 4 shows an example network diagram including a plant monitoring computing platform and FIG. 5 shows an example of the plant comprising a data collection platform connected to a control platform.

FIG. 4 shows an example network diagram comprising a plant monitoring computing platform 410. The plant monitoring computing platform 410 may be connected, via a network 420, to a plant 430, an operator office 440, and external servers 450. The plant 430 may, for example, be configured to perform the catalytic dehydrogenation process of FIG. 1 and/or the processes shown in FIGS. 2 and 3.

The plant monitoring computing platform 410 may be one or more computing devices, such as one or more servers (e.g., a cloud computing platform) configured to receive plant data and determine catalyst health. Computing devices may comprise any form of device configured with one or more processors and/or memory storing instructions that, when executed by the processor, perform one or more steps. The plant monitoring computing platform may be configured to receive, from the plant 430, plant data comprising operational data such as sensor measurements. The plant monitoring computing platform may be configured to process the received plant data, such as by performing error detecting routines, organizing the plant data, reconciling the plant data with a template or standard, and/or store the received plant data, as discussed in greater detail below. Based on the plant data, the plant monitoring computing platform may be configured to determine an indication of the health of a catalyst. Though the plant monitoring computing platform 410 is depicted as a single element in FIG. 4, it may be a distributed network of computing devices located in a plurality of different locations. For example, the plant monitoring computing platform 410 may operate on a plurality of different servers distributed worldwide, the plant 430 may be in a first town, and the operator office 440 may be in a second town. As another example, the operator office 440 and the plant monitoring computing platform 410 may be in the same location and/or part of the same organization, such that the same computing device acting as the plant monitoring computing platform 410 may operate on behalf of the operator office 440. The plant monitoring computing platform 410 may comprise instructions executed by one or more processors. For example, the plant monitoring computing platform 410 may be an executable file.

The plant monitoring computing platform 410 may comprise a plurality of different mechanisms by which received plant data may be processed and interpreted. The plant monitoring computing platform 410 may process and/or analyze received plant data. For example, computing devices of the plant monitoring computing platform 410 may be configured to execute code that compares all or portions of plant data to threshold values and/or ranges. Machine learning algorithms may be used to process and/or interpret received plant data. For example, the plant monitoring computing platform 410 may store and use old measurements to teach a machine learning algorithm acceptable ranges for plant data, and new plant data may be input into the machine learning algorithm to determine if an undesirable plant condition exists. Manual review by experts may be performed to process and/or interpret received plant data. For example, a certain range of plant data (e.g., unexpectedly high numbers) may require manual review by an expert (e.g., a plant employee) using a computing device associated with the plant monitoring computing platform 410.

The plant monitoring computing platform 410 may be configured such that, if a measurement (e.g., in plant data)

deviates from the equilibrium conditions, a notification may be sent by the plant monitoring computing platform 410. For example, the plant monitoring computing platform 410 may be configured to determine a difference between a measurement and equilibrium conditions and, if the difference satisfies a threshold, send a notification. Such equilibrium conditions may be based on external data received from the external servers 450 and/or additional plant data received from the operator office 440. For example, temperature measurements may be analyzed in view of the ambient temperature of the plant 430 as determined via external data received from the external servers 450 and/or as determined via a thermometer at the operator office 440. The notification may, for example, be a text message, e-mail, or any other form of communication over the network 420.

Additionally or alternatively to sending a notification, the plant monitoring computing platform 410 may be configured to cause the plant 430 to perform an action. The plant monitoring computing platform 410 may be configured to cause the plant 430 to, for example, open or close one or more valves and/or drains, change the operating parameters of pumps, feed switchers, gates, and/or sprayers, or similar actions. The plant monitoring computing platform 410 may be configured to trigger an alarm at the plant 430, e.g., when unsafe operating conditions are determined. The plant monitoring computing platform 410 may cause the plant 430 to take actions which require manual intervention, such as initiating a process in which catalyst may be, in whole or in part, replaced.

The plant monitoring computing platform 410 may be configured to make determinations regarding the activity of a catalyst. The plant 430 may cease to be profitable if, for example, the yield of product via a catalyst drops below a threshold due to decreases in the activity of the catalyst. The plant monitoring computing platform 410 may, for example, determine that a catalyst will drop below a predetermined profitability limit in a time period (e.g., in an hour, in two weeks). The plant monitoring computing platform 410 may send a notification corresponding to such a determination. The plant monitoring computing platform 410 may cause computing devices associated with the operator office 440 to order additional catalyst from a supplier and/or send a notification to operators of the plant 430 that the catalyst must be replaced.

The network 420 may be a public network, a private network, or a combination thereof that communicatively couples the plant monitoring computing platform 410 to other devices. Communications between devices such as the computing devices of the plant 430 and the plant monitoring computing platform 410, may be packetized or otherwise formatted in accordance with any appropriate communications protocol. For example, the network 420 may comprise a network configured to use Internet Protocol (IP).

The plant 430 may be any of various types of chemical and petrochemical manufacturing or refining facilities. The plant 430 may be configured with one or more computing devices that monitor plant parameters and report such measurements to the plant monitoring computing platform 410. The plant 430 may comprise sensors that report measurements to the plant monitoring computing platform 410 via the network 420. The plant 430 may additionally or alternatively conduct tests (e.g., lab tests producing lab data), which may be sent to the plant monitoring computing platform 410. Such measurements may relate to the temperature, pressure, flow rate, composition, molecular weight, viscosity, pH, color, and/or the specific weight of liquids, gases, or solids (e.g., the temperature of a burner or an inlet valve). Additionally or alternatively, such measurements may comprise a ratio of dihydrogen (H2) to hydrocarbons and/or a measurement of hydrogen sulfide (H2S) levels. Techniques such as gas chromatography may be used to analyze such compounds. Measurements related to the plant 430, such as the amount of power used (e.g., by a machine) or the like may additionally or alternatively be measured. Reporting of such measurements may occur on a periodic basis (e.g., every ten seconds, every hour, for each plant cycle) or a continual basis.

The operator office 440 may be configured to, via one or more computing devices of the operator office 440, receive measurements and send such measurements to the plant monitoring computing platform 410, configure the plant 430, and/or communicate with and configure the plant monitoring computing platform 410. The operator office 440 may be where plant data is determined, such that plant data may originate from both or either the plant 430 and the operator office 440. The operator office 440 may be enabled to make plans with regard to the plant 430 based on output from the plant monitoring computing platform 410.

Figure 5:
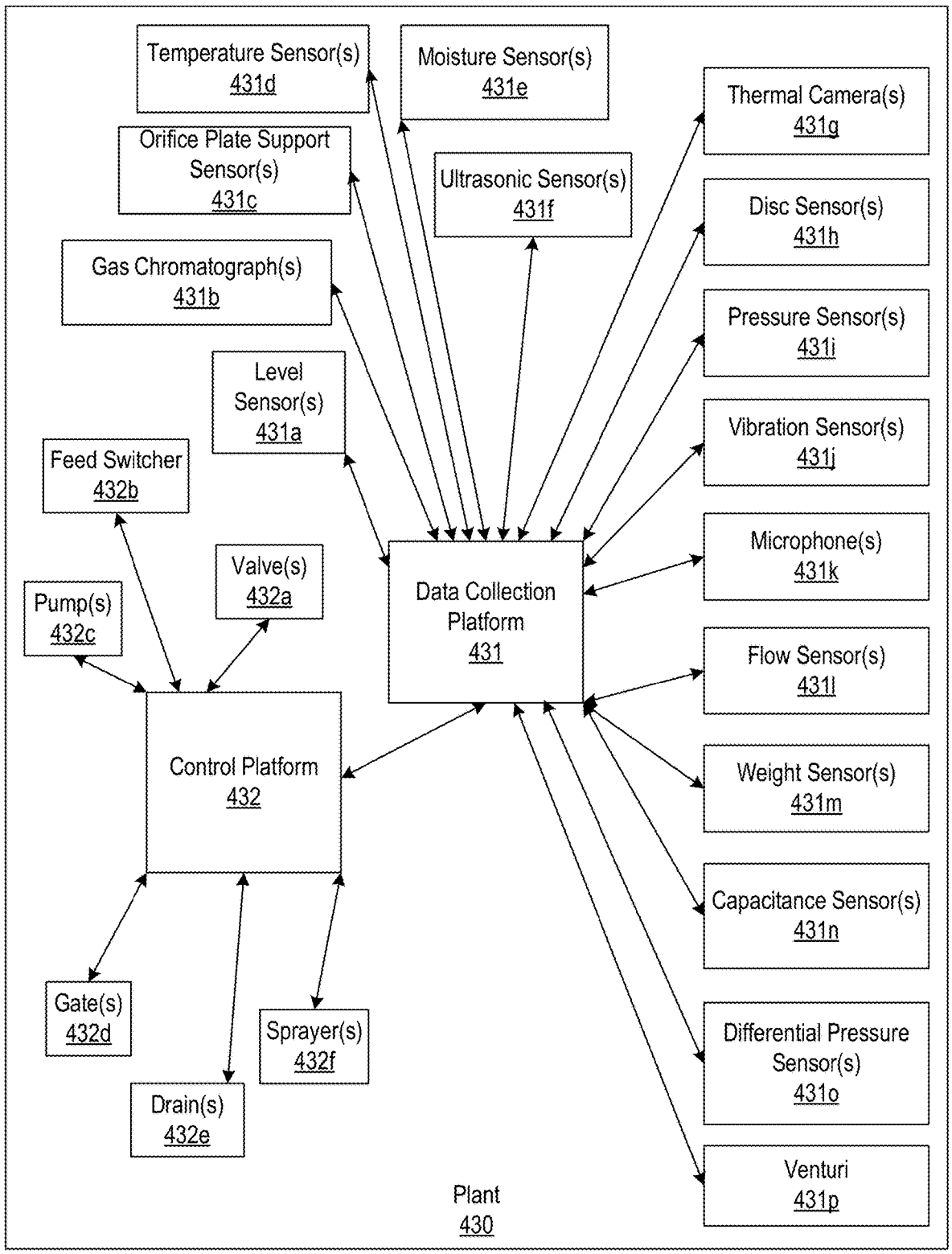

FIG. 5 shows an example of the plant 430 comprising a data collection platform 431 connected to a control platform 432. The data collection platform 431 is connected to sensors 431*a-p*. The control platform 432 is connected to controllable devices 432*a-f*. The sensors and controllable devices depicted in FIG. 5 are examples, any number or type of sensors and/or controllable devices may be implemented, whether or not connected to the data collection platform 431 or the control platform 432.

The data collection platform may be configured to collect plant data from one or more sensors and/or controllable devices and transmit that information, e.g., to the plant monitoring computing platform 410. Such sensors may comprise, for example, level sensors 431*a*, gas chromatographs 431*b*, orifice plate support sensors 431*c*, temperature sensors 431*d*, moisture sensors 431*e*, ultrasonic sensors 431*f*, thermal cameras 431*g*, disc sensors 431*h*, pressure sensors 431*i*, vibration sensors 431*j*, microphones 431*k*, flow sensors 431*l*, weight sensors 431*m*, capacitance sensors 431*n*, differential pressure sensors 431*o*, and/or venturi 431*p*. The data collection platform may additionally or alternatively be communicatively coupled to the control platform 432 such that, for example, the data collection platform 431 may receive, from the control platform 432 and/or any of the controllable devices 432*a-f*, operating information. The controllable devices 432*a-f* may comprise, for example, valves 432*a*, feed switchers 432*b*, pumps 432*c*, gates 432*d*, drains 432*e*, and/or sprayers 432*f*.

Figure 6:
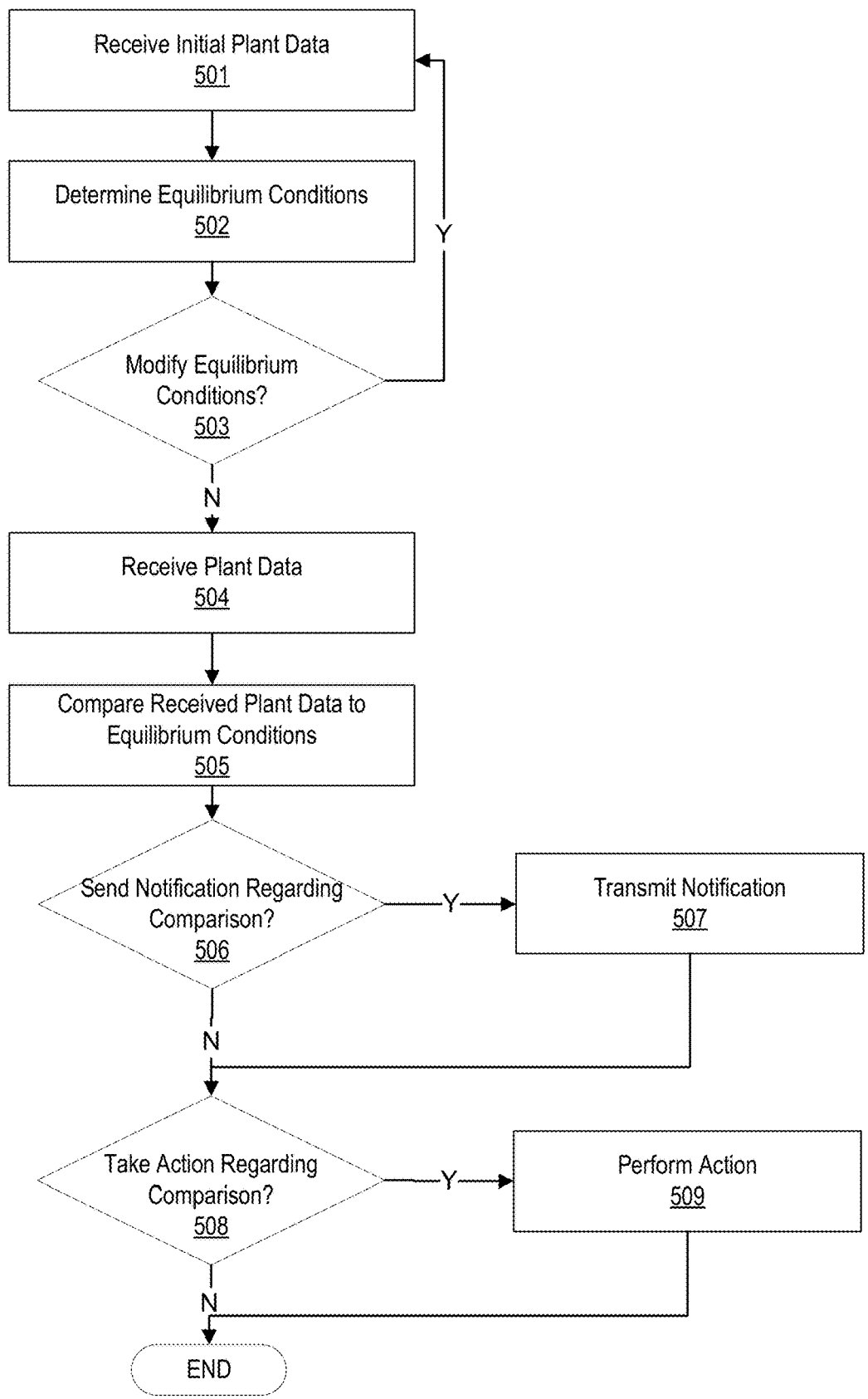
FIG. 6 shows an example flow chart in accordance with features described herein.

FIG. 6 shows a flowchart that may be performed with respect to the plant monitoring computing platform. In step 501, the plant monitoring computing platform (e.g., plant monitoring computing platform 410) may receive initial plant data from a plant (e.g., plant 430). The initial data may comprise any measurements or information corresponding to one or more plants, such as sensor measurements and/or lab data.

As part of the receipt of any plant data, the plant monitoring computing platform may be configured to process and/or analyze the data. The plant monitoring computing platform may, for example, execute an error correction algorithm to correct errors in received plant data. Based on determining only certain plant data is needed, a first portion of the received plant data (e.g., the certain plant data) may be stored, whereas a second portion of the received plant data (e.g., other plant data) may be discarded. Processing may comprise determining a reliability of received plant data. For example, impossible measurements (e.g., a temperature reading from a sensor indicating that a substance is hotter than the surface of the Sun) may be determined unreliable and potentially indicative of a malfunctioning sensor. As another example, based on previous measurements indicating a downward temperature trend, a most current measurement which indicates an extremely high temperature may be considered unreliable until multiple such measurements are received from a plant.

In step 502, based on the initial plant data received, equilibrium conditions may be determined for a plant. Equilibrium conditions may comprise any acceptable values, ranges of values, and/or criterion that indicate target operating conditions for a plant. For example, equilibrium conditions may be targeted measurements that indicate that a plant is successfully and/or profitably producing a product and that all machines and substances (e.g., catalysts) are functioning properly and are otherwise in good health. Equilibrium conditions may be determined based on the received initial plant data such that, for example, if temperature values received as part of initial plant data reported temperatures between a particular temperature range (e.g., between 1100 and 1200 degrees Fahrenheit), then this range may be considered equilibrium conditions for the temperature values. An equilibrium condition need not suggest that all measurements outside of particular equilibrium values/ranges/criterion indicate a malfunction. For example, an increase in temperature of an outlet valve—which may be detected by a temperature sensor attached to or otherwise monitoring that outlet valve—may be but one indicator of malfunction, but might not itself be dispositive of a malfunction. As such, equilibrium conditions may be conditional and/or may account for numerous portions of plant data. The equilibrium conditions may correspond to use of a catalyst, such that a first set of equilibrium conditions may correspond to a fresh catalyst, a second set of equilibrium conditions may correspond to a moderately used catalyst, and the like. Thus, equilibrium conditions for fresh catalyst need not be the same as equilibrium conditions for a well-used catalyst.

Equilibrium conditions may be based on the accuracy and/or fidelity of the initial plant data received. The initial data received in step 501 may comprise data that relates to break-in periods, such as a period when a catalyst is stabilized and/or when machines are warmed up, and the received data may be appropriately discounted based on its association with a break-in period. Discounting may comprise, for example, weighting plant data less in comparison to other plant data. For example, it can take three to four catalyst regeneration cycles for baseline catalyst properties to be measured. As such, the plant monitoring computing platform may be configured to identify such conditions and discard and/or discount such initial plant data.

Equilibrium conditions may comprise a flowchart or flowsheet comprising equilibrium states and/or models. For example, the equilibrium conditions may be a flowchart such that certain data is analyzed in the event that the outlet valve temperature exceeds a first predetermined value, but that other data is analyzed in the event that the outlet valve temperate is below the first predetermined value.

Equilibrium conditions may relate to product yield. For example, equilibrium conditions may relate to conditions in which a particular quantity of product may be produced (e.g., ten tons per hour). As another example, equilibrium conditions may relate to the profitability of product yield, such that the equilibrium conditions relate to an operational status of the plant where a certain amount of profit is made (e.g., where $100 per ton profit is made).

Determining equilibrium conditions may be, in whole or in part, effectuated using a machine learning algorithm. A machine learning algorithm may implement a neural network or similar computing device structure to allow one or more computing devices to learn based on data and later make classifications based on the learning. The initial plant data received may be input into a machine learning algorithm to allow the algorithm to determine associations and appropriate weightings for the data. Such learning may be supervised such that, for example, undesirable data is appropriately tagged as undesirable (e.g., as indicative of a plant issue) by an operator of the machine learning algorithm. As such, the equilibrium need not be a particular range, but may instead represent the learning of the machine learning algorithm. The equilibrium conditions may thus be reflected by the decision-making of the machine learning algorithm.

Determining equilibrium conditions may be based on the configuration of a plant. While two different plants may report the same or similar types of plant data, the data itself may vary based on the configuration of each individual plant. For example, different plant machinery may exhibit different ranges of temperatures, flow rates, and other measurable conditions. Such information may be used to determine equilibrium conditions. As a particular example, well-insulated equipment may exhibit higher temperatures than poorly-insulated equipment, such that both may exhibit different temperature profiles under similar operating conditions.

Determining equilibrium conditions may involve, in whole or in part, manual entry of equilibrium conditions by a plant operator. For example, based on mechanical and/or safety limitations of machines in a plant, a plant operator may specify that a certain reactor temperature should not exceed a certain value under any circumstances. As another example, a desired chemical reaction involving a catalyst may never occur under a threshold temperature (e.g., 100° F.), such that the threshold temperature (e.g., 100° F.) may be established as the absolute lowest temperature for a particular reactor using the catalyst.

Determining equilibrium conditions may involve, in whole or in part, use of plant data from other plants. Certain measurements may be standardized across plants such that, for example, a certain catalyst, when used properly, must remain within a certain range of temperatures regardless of equipment or ambient conditions. Based on catalyst temperature ranges observed from other plants, the equilibrium conditions for a first plant may be determined. Use of multiple plants' data may additionally or alternatively be used to improve equilibrium condition fidelity. For example, the best range of reactor temperatures may be determined by analyzing multiple (e.g., hundreds of) different reactors associated with multiple (e.g., tens of) plants distributed worldwide, rather than use of measurements only from reactors from a single plant.

In step 503, the plant monitoring computing platform may determine whether to modify the equilibrium conditions. The plant monitoring computing platform may determine whether to modify the equilibrium conditions based on a comparison of the equilibrium conditions and data received from a plant and/or external data received from external servers (e.g., external servers 450). The plant monitoring computing platform may be configured to evaluate the accuracy of the equilibrium conditions and, if the equilibrium conditions do not have a level of accuracy that meets a threshold, the plant monitoring computing platform may be configured to collect additional data such that the equilibrium conditions may be revised. If the plant monitoring computing platform determines to modify the equilibrium conditions, the flow chart may return to step 501. Otherwise, the flow chart may proceed to step 504.

One example reason that the equilibrium conditions may be modified is to improve the fidelity of the equilibrium conditions. The initial plant data received in step 501 may be accurate but may be limited: for example, the initial plant data received in step 501 may comprise only one set of measurements, such that any equilibrium conditions determined from the initial plant data may be highly unreliable. The plant monitoring computing platform may require a threshold number of sets of measurements to determine equilibrium conditions, such that the equilibrium conditions may be modified based on determining that a number of sets of measurements received does not satisfy the threshold. Based on determining that the fidelity of the equilibrium conditions is inadequate, the flow chart may return to step 501 so that additional plant data may be received.

In step 504, plant data may be received. The plant data received in step 501 may be in a same or similar format as the initial plant data received in step 504. As such, the plant data in step 504 may additionally or alternatively be used to modify the equilibrium conditions determined in step 502.

In step 505, plant data may be compared to the equilibrium conditions determined in step 502. The comparison may comprise determining whether the plant data received in step 504 falls within a range of the equilibrium conditions, is one of a predetermined number of acceptable values, or other similar comparison methods. A degree of similarity to the equilibrium conditions (e.g., a delta value between the measured value and the equilibrium value) may be determined. The equilibrium conditions may comprise a conditional test, such that the comparison may comprise testing the plant data using the conditional test.

The plant data compared in step 505 need not comprise only the plant data received in step 504, but also previously-received plant data. For example, a weighted average of the plant data received in step 504 and previously received plant data may be determined, and that weighted average may be compared to the equilibrium conditions. In this manner, small fluctuations in measurements may be smoothed out and/or trends may be identified.

The plant monitoring computing platform may, based on the plant data, determine predicted future plant data and compare such predicted future plant data with the equilibrium conditions. For example, current temperature measurements may be rapidly rising such that future temperature measurements will likely indicate a problem at a plant. Accordingly, the plant monitoring computing platform may identify the rapidly rising conditions and compare a predicted, higher temperature with the equilibrium conditions.

In step 506, the plant monitoring computing platform may determine whether the comparison in step 505 indicates that a notification should be transmitted. A notification need not suggest a problem but may indicate, for example, that a catalyst may soon need to be replenished and/or replaced, that a machine may be wearing out, that an operating condition of the plant need to be modified for better performance, the health of all or a part of a plant, or the like. If the plant monitoring computing platform determines to transmit a notification, the flow chart may proceed to step 507 and send the notification and proceed to step 508. Otherwise, the flow chart may proceed to step 508.

The comparison of the plant data and the equilibrium conditions may relate to all or a portion of the plant. The comparison may indicate that all or a part of a catalyst is deactivated, that all or a portion of one or more reactors has a problem, potential issues with the flow rate of a catalyst or a reactant, undesirable build-up on all or part of a catalyst, issues with input or output, or the like. The comparison need not indicate a binary condition (e.g., the presence or absence of a problem), but may also suggest a measurement or calculation (e.g., an indication of the health of the catalyst, a percentage of deactivated catalyst, a time duration associated with the health of the catalyst). The notification may include information relating to the comparison of the plant data to the equilibrium conditions (e.g., that all or a portion of one or more reactors has a problem, identified potential issues with the flow rate of a catalyst or a reactant, undesirable build-up on all or part of a catalyst, identified issues with input or output, or the like).

As an illustrative example of steps 504 through 506, the plant data received by the plant monitoring computing platform may comprise reactor inlet temperatures as measured five times over the course of ten minutes. The measurements may be, for example, 701, 702, 705, 706, and 709 degrees Fahrenheit, wherein the temperature measurements are compared to some reference temperature (e.g., $\Delta\_$ values, wherein the measurements are compared to a baseline reference measurement). The plant monitoring computing platform may compare the reactor inlet temperatures to a determined equilibrium range that permits the measured reactor inlet temperatures to be anywhere from 690 to 710 degrees Fahrenheit, suggesting no immediate concern. The plant monitoring computing platform may nonetheless a predicted future reactor inlet temperature of 725 degrees Fahrenheit and compare the predicted future reactor temperature against the equilibrium range. Such a condition may indicate an issue, warranting the transmission of a notification corresponding to, for example, the trend in the heat increase and/or a potential trend in catalyst health.

As another example of steps 504 through 506, the weighted average of received inlet temperatures may be divided by the start-of-run weighted average of inlet temperatures, wherein the inlet is associated with introducing a catalyst to a reactant (e.g., the inlet is used to send a catalyst into a chamber with a reactant, the inlet is used to send the reactant into a chamber with the catalyst, or the like). This value may suggest the health of the catalyst in the plant. As such, the notification need not suggest that the catalyst has a problem, but may rather may indicate the health of the catalyst in the plant.

As yet another example of steps 504 through 506, a machine learning algorithm may be provided plant data. The machine learning algorithm may have learned, from the initial plant data, to detect particular circumstances (e.g., growth of a deactivated portion of a catalyst) of the plant. The machine learning algorithm may determine, based on a comparison of the plant data to one or more tests, that a first reactor of the plant is operating normally, but a second reactor of the plant has a growing deactivated portion of a catalyst.

In step 507, the plant monitoring computing platform may transmit a notification. The notification may be to one or more computing devices (e.g., of the plant 430, the operator office 440, or the like), to a plant operator (e.g., causing a notification to be sent via a text message, application alert, or the like to a cell phone associated with the plant operator), or the like.

The plant monitoring computing platform may be configured to report, via a notification, one or more measurements, characterizations, and/or calculations based on the plant data. The plant monitoring computing platform may be configured to trigger periodic notifications of the health of a catalyst. For example, a notification may simply indicate the health of one or more catalysts and may be sent to a plant operator on an hourly basis. Other examples of information that may be sent in a notification include an estimated hydrogen/hydrocarbon ratio, a characterization of a reactor operating status (e.g., "needs attention"), a calculated ratio of an active portion of a catalyst to a deactivated portion of a catalyst, or other measurements, characterizations, and/or calculations.

For example, in the context of catalyst health, the plant monitoring computing platform may be configured to periodically transmit (e.g., to one or more computing devices at the plant, operator office, and/or one or more external servers) a notification comprising a calculated catalyst health associated with one or more reactors at a plant. The calculated health may comprise a ratio or percentage, such as a division of a current quantity of active catalyst as by an originally active quantity of catalyst. The notification may be daily such that, on a daily basis, a plant operator may receive an indication of the current percentage of active catalyst. The notification may further comprise an indication of a projected consumption rate of the catalyst (e.g., an indication that the catalyst health will drop by 1% every week, and/or an indication that the catalyst will need to be replaced in six months). Once the percentage of active catalyst satisfies a threshold (e.g., 50% or below), the notification may indicate that the plant operator should replenish or otherwise replace the catalyst. The threshold may be based on profit margin. For example, the threshold may be based on an amount of profit associated with the product (e.g., $50 per ton), such that, when the percentage of active catalyst satisfies the threshold, the amount of profit associated with the product has become undesirably low.

The plant monitoring computing platform may be additionally or alternatively configured to send notifications associated with, based on the comparison in step 505, the detection of feed poisons, miss operations, plant upsets, and/or other problems. Such notifications may be prioritized over other notifications. For example, while some notifications may be messages, a notification of a problem may trigger an alarm (e.g., causing an alarm to sound at the plant).

The plant monitoring computing platform may be configured to provide notifications relating to improving plant yield and/or production volume. For example, based on the analysis of plant data, the plant monitoring computing platform may determine that modification of an operating parameter would not harm plant effectiveness and may improve the yield and/or production volume of the plant. Based on such a determination, the plant monitoring computing platform may send a corresponding notification to a plant operator.

In step 508, the plant monitoring computing platform may, in response to the comparison, determine whether to cause the plant to take an action. The reasons why action may be taken may be the same or similar to that of providing a notification. For example, the plant monitoring computing platform may determine that the amount of active catalyst remaining satisfies a threshold and determine to take an action (e.g., initiating replacement of the catalyst) on that basis. Such actions may be any change to controllable devices (e.g., controllable devices 432*a-f*) of the plant. As another example, the plant monitoring computing platform may determine that a temperature reading for a device satisfies a threshold and, on that basis, determine to open a ventilation duct to cool the measured device. As yet another example, the plant monitoring computing platform may, based on an unsafe condition detected based on the plant data, cause the plant to sound an alarm. The action may relate to a notification, such that, for example, the plant monitoring computing platform may send a notification that it is causing the plant to perform an action. If the plant monitoring computing platform decides to take the action, it may do so in step 509. Otherwise, the flow chart may end.

Conclusion

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps illustrated in the illustrative figures may be performed in other than the recited order, and one or more depicted steps may be optional in accordance with aspects of the disclosure.

What is claimed is:

1. A method comprising:
   determining, by a computing device, equilibrium conditions for a plant, wherein the equilibrium conditions are associated with a catalyst used by the plant and with a reactant to produce a product, and wherein the equilibrium conditions relate to target operating conditions associated with the catalyst;
   receiving, via a network, plant data from a sensor associated with the plant, wherein the plant data comprises a measurement associated with the catalyst;
   comparing the plant data to the equilibrium conditions, wherein comparing the plant data to the equilibrium conditions comprises comparing the measurement to the target operating conditions associated with the catalyst;
   determining, based on comparing the equilibrium conditions to the plant data, a notification; and
   transmitting, by the computing device, the notification.

2. The method of claim 1, wherein the measurement corresponds to an inlet of the plant, and wherein the inlet is configured to introduce the catalyst to the reactant.

3. The method of claim 1, wherein the notification comprises an indication comparing a first active portion of the catalyst at a first time to a second active portion of the catalyst at a second time.

4. The method of claim 1, further comprising:
   receiving, from the sensor, initial plant data, wherein the equilibrium conditions are based on the initial plant data.

5. The method of claim 4, further comprising:
   determining a first portion of the initial plant data corresponding to a time period when the catalyst is stabilizing;
   determining a second portion of the initial plant data corresponding to a second time period when the catalyst has stabilized; and
   discounting the first portion of the initial plant data.

6. The method of claim 1, wherein comparing the plant data to the equilibrium conditions further comprises comparing the measurement to the target operating conditions associated with fresh catalyst.

7. The method of claim 1, further comprising:
   receiving second plant data associated with a second plant, wherein the equilibrium conditions are based on the second plant data.

8. The method of claim 1, wherein the notification corresponds to one of a plurality of reactors of the plant.

9. The method of claim 1, wherein the plant data further comprises lab data corresponding to tests associated with one or more of: the catalyst, the reactant, or the product.

10. The method of claim 1, wherein determining the equilibrium conditions are based on one or more of: equipment installed at the plant, the product, the reactant, or a production volume of the plant.

11. A computing device comprising:
one or more processors; and
memory storing instructions that, when executed by the one or more processors, cause the computing device to:
determine equilibrium conditions for a plant, wherein the equilibrium conditions are associated with a catalyst used by the plant and with a reactant to produce a product, and wherein the equilibrium conditions relate to target operating conditions associated with the catalyst;
receive, via a network, plant data from a sensor associated with the plant, wherein the plant data comprises a measurement associated with the catalyst;
compare the plant data to the equilibrium conditions, wherein comparing the plant data to the equilibrium conditions comprises comparing the measurement to the target operating conditions associated with the catalyst;
determine, based on comparing the equilibrium conditions to the plant data, a notification; and
transmit the notification.

12. The computing device of claim 11, wherein the instructions, when executed by the computing device, further cause the computing device to:
receive, from the sensor, initial plant data, wherein the equilibrium conditions are based on the initial plant data.

13. The computing device of claim 12, wherein the instructions, when executed by the computing device, further cause the computing device to:
determine a first portion of the initial plant data corresponding to a time period when the catalyst is stabilizing;
determine a second portion of the initial plant data corresponding to a second time period when the catalyst has stabilized; and
discount the first portion of the initial plant data.

14. The computing device of claim 11, wherein the instructions, when executed by the computing device, further cause the computing device to:
receive second plant data associated with a second plant, wherein the equilibrium conditions are based on the second plant data.

15. The computing device of claim 11, wherein the plant data further comprises lab data corresponding to tests associated with one or more of: the catalyst, the reactant, or the product.

16. A system comprising:
a plant configured to introduce a catalyst to a reactant to produce a product; and
a computing device comprising:
one or more processors; and
memory storing instructions;
wherein the plant is configured to transmit, to the computing device and via a network, plant data comprising a measurement associated with the catalyst; and
wherein the instructions, when executed by the one or more processors, cause the computing device to:
determine equilibrium conditions for the plant, wherein the equilibrium conditions are associated with the catalyst, and wherein the equilibrium conditions relate to target operating conditions associated with the catalyst;
receive plant data from a sensor associated with the plant, wherein the plant data comprises a temperature measurement associated with the catalyst;
compare the plant data to the equilibrium conditions, wherein comparing the plant data to the equilibrium conditions comprises comparing the temperature measurement to the target operating conditions of the catalyst;
determine, based on comparing the equilibrium conditions to the plant data, a notification; and
transmit the notification.

17. The computing device of claim 16, wherein the instructions, when executed by the computing device, further cause the computing device to:
receive, from the sensor, initial plant data, wherein the equilibrium conditions are based on the initial plant data.

18. The computing device of claim 17, wherein the instructions, when executed by the computing device, further cause the computing device to:
determine a first portion of the initial plant data corresponding to a time period when the catalyst is stabilizing;
determine a second portion of the initial plant data corresponding to a second time period when the catalyst has stabilized; and
discount the first portion of the initial plant data.

19. The computing device of claim 16, wherein the instructions, when executed by the computing device, further cause the computing device to:
receive second plant data associated with a second plant, wherein the equilibrium conditions are based on the second plant data.

20. The computing device of claim 16, wherein the plant data further comprises lab data corresponding to tests associated with one or more of: the catalyst, the reactant, or the product.

* * * * *